United States Patent [19]

Cymbaluk et al.

[11] Patent Number: 5,039,638
[45] Date of Patent: Aug. 13, 1991

[54] CONVERSION OF SPENT BUTANE ISOMERIZATION CATALYSTS TO PENTANE ISOMERIZATION CATALYSTS

[75] Inventors: Ted H. Cymbaluk; Gerhard P. Nowack; Marvin M. Johnson, all of Bartlesville, Okla.

[73] Assignee: Phillips Petroleum Company, Bartlesville, Okla.

[21] Appl. No.: 593,822

[22] Filed: Oct. 5, 1990

[51] Int. Cl.⁵ .............................................. B01J 38/46
[52] U.S. Cl. ...................................... 502/36; 502/230
[58] Field of Search ................................. 502/36, 230

[56] References Cited

U.S. PATENT DOCUMENTS

| | | | |
|---|---|---|---|
| 3,449,264 | 6/1969 | Myers | 252/441 |
| 3,969,267 | 7/1976 | McVicker | 502/36 |
| 4,014,948 | 3/1977 | Myers | 260/666 P |
| 4,069,268 | 1/1978 | Siskin et al. | 502/36 |
| 4,612,293 | 9/1986 | Johnson | 502/28 |
| 4,644,090 | 2/1987 | Johnson | 585/749 |

OTHER PUBLICATIONS

"Catalyst Manufacture", by Alvin B. Stiles, p. 58, Marcel Dekker, Inc., 1983.

Primary Examiner—Patrick P. Garvin
Assistant Examiner—Brent M. Peebles
Attorney, Agent, or Firm—K. K. Brandes

[57] ABSTRACT

A spent butane isomerization catalyst which contains platinum and chlorine on alumina is converted to an active n-pentane isomerization catalyst by processes comprising fluorination (preferably with dissolved HF or NH₄HF) and calcination (before and/or after the fluorination step). The thus-treated catalysts are used for isomerizing n-pentane to isopentane.

21 Claims, No Drawings

CONVERSION OF SPENT BUTANE ISOMERIZATION CATALYSTS TO PENTANE ISOMERIZATION CATALYSTS

This invention relates to isomerization processes and catalysts therefor. In one aspect, this invention relates to the rejuvenation of spent isomerization catalysts. In another aspect, this invention relates to the conversion of spent butane isomerization catalysts to active pentane isomerization catalysts.

BACKGROUND OF THE INVENTION

Catalysts comprising platinum on alumina are useful for the isomerization of saturated hydrocarbons. These catalysts are subject to deactivation as a result of prolonged usage for a variety of reasons. For example, the physical state of the platinum can change under long term exposure to isomerization conditions. Further, contaminants in the feed over an extended period of time tend to deactivate the catalysts. Moreover, carbonization of the catalyst and/or loss of activating catalyst adjuvants can also cause loss of catalyst isomerization activity.

Typically, "spent" (i.e., substantially deactivated) catalysts are processed to extract, separate and recover the platinum values therefrom. The recovered platinum values are then used to prepare fresh catalyst. Such a regeneration process is, however, an expensive operation because of the number of steps involved, the amount of reagents required, etc. A process to readily convert a substantially deactivated isomerization catalyst to a once again active isomerization catalyst would, therefore, be of great benefit to those practicing in the field of hydrocarbon isomerizations.

SUMMARY OF THE INVENTION

It is an object of this invention to produce an active pentane isomerization catalyst from a deactivated butane isomerization catalyst. Another object of this invention is the isomerization of pentanes employing a regenerated butane isomerization catalyst. Other objects and advantages will become apparent from the detailed description of the invention and the appended claims.

In accordance with this invention, a process for converting a substantially deactivated butane isomerization catalyst comprising platinum and chlorine (as chloride) on an alumina support to an active catalyst for isomerizing n-pentane comprises the steps of:

(1) calcining said substantially deactivated butane isomerization catalyst (hereinafter referred to as "spent catalyst") at a temperature in the range of about 500° C. to about 700° C. for a time sufficient to remove a substantial portion of chlorine (and also of carbon deposits) contained in said spent catalyst;

(2) cooling the calcined spent catalyst obtained in step (1) to a temperature below about 500° C.;

(3) treating the cooled calcined spent catalyst obtained in step (2) with a solution of at least one effective fluorinating agent under such conditions as to introduce fluorine (as fluoride-containing ions) into said cooled calcined spent catalyst; and (4) drying the fluorinated spent catalyst obtained in step (3) under such conditions as to obtain a substantially dry fluorinated catalyst which is active as a catalyst for isomerizing n-pentane to isopentane (2-methylbutane).

Also in accordance with this invention (yet less preferred), a process for converting a substantially deactivated butane isomerization catalyst comprising platinum and chlorine (as chloride) on an alumina support to an active catalyst for isomerizing pentanes comprises the steps of:

(A) treating said substantially deactivated butane isomerization catalyst (hereinafter referred to "spent catalyst") with a solution of an effective fluorinating agent under such conditions as to introduce fluorine (as fluoride-containing ions) into the spent catalyst;

(B) heating the fluorinated spent catalyst obtained in step (A) to a temperature below 500° C. so as to at least partially dry the fluorinated spent catalyst obtained in step (A); and (C) calcining the at least partially dried fluorinated spent catalyst obtained in step (B) at a temperature in the range of from about 500 to about 700° C. for a time sufficient to remove a substantial portion of chlorine (and also carbon deposits) contained in the dried fluorinated spent catalyst so as to obtain a fluorinated spent catalyst which is active as a catalyst for isomerizing n-pentane to isopentane.

Further in accordance with this invention, there are provided active n-pentane isomerization catalysts prepared by one of the above-described reactivation processes comprising steps (1)–(4) or steps (A)–(C).

Still further in accordance with this invention, there are provided processes for isomerizing n-pentane to isopentane employing a catalyst which has been prepared by one of the above-described reactivation processes comprising steps (1)–(4) or steps (A)–(C), wherein a n-pentane containing feed is contacted with the catalyst under effective isomerization conditions.

DETAILED DESCRIPTION OF THE INVENTION

Any substantially deactivated (spent) butane isomerization catalyst which contains Pt, Cl and alumina can be used in step (1) or (A) of the reactivation processes of this invention. Fresh (unused) butane isomerization catalysts which catalyze the conversion of n-butane to isobutanes are well known. They can be prepared by processes described in the patent literature, such as in U.S. Pat. Nos. 3,449,264 and 4,014,948. Butane isomerization catalysts are also commercially available, e.g., from UOP, Inc., Des Plaines, Ill, and from the Catalyst and the Chemicals Division of Engelhard Corporation, Newark, NJ. Generally, these catalysts contain about 0.01–10 (preferably about 0.1–1) weight-% Pt and about 1–10 (preferably about 2–6) weight-% Cl. The spent butane isomerization catalyst which is used in step (1) or (A) of the reactivation processes of this invention is one of the above-described fresh catalyst which has been employed in a butane isomerization process and has become substantially deactivated (to the extent that the catalyst no longer satisfies the required conversion/selectivity requirements for the butane isomerization process). The spent catalyst has not been washed (for chloride removal) with water or an aqueous solution prior to step (1) or step (A). The spent catalyst generally contains about 0.01–10 (preferably about 0.1–1) weight-% Pt and about 1–10 (preferably about 1–5) weight-% Cl.

Calcining step (1) of the preferred catalyst treating processes of this invention can be carried out by heating the spent butane isomerization catalyst at about 500–800° C., preferably at about 600–750° C., so as to remove a substantial portion (i.e., at least about 50%) of chlorine contained in the spent catalyst. Preferably, also a significant portion of carbon deposits on the spent catalyst (which generally contains about 0.05–0.5 weight-% C) is removed during calcining. Preferably, about 50–99% (more preferably about 0–98%) of the chlorine is removed in step (1). Generally, this will require a heating time of at least about 5 minutes, and may require up to about 40 hours (especially when heated at a low temperature). Preferably, a heating time of about 10 minutes to about 10 hours, more preferably about 15 minutes to 60 minutes is employed. Heating step (1) can be carried out in an oxidizing atmosphere (such as air) or in an inert atmosphere (such as $N_2$), preferably in a free oxygen containing gas atmosphere. The calcining operation can be carried out in any of the well known heating vessels, preferably in a rotary calciner. Gaseous HCl is generated during the calcining step and should be removed (preferably by scrubbing with aqueous NaOH) before the exiting gas is released into the atmosphere.

Cooling step (2) can be carried out in any suitable manner (in an oxidizing or inert atmosphere). It can be done in the calcination reactor while heating is discontinued. Or it can be done while the calcined spent catalyst is transferred from the calcination vessel to the fluorinating vessel. Generally, the hot calcined catalyst is cooled from the calcination temperature to below about 500° C., preferably to about 10–90° C.

Fluorinating step (3) can be carried out in any suitable manner in any suitable vessel. The cooled calcined spent catalyst is contacted with a solution (preferably aqueous) of an effective fluorinating agent, which can be HF, $NH_4F$, $NH_4HF_2$ (ammonium bifluoride), $NH_3RF$, $NH_2R_2F$, $NHR_3F$, $NR_4F$ or mixtures thereof, wherein R is a hydrocarbyl radical (preferably alkyl radical) containing 1–6 carbon atoms; preferably HF or $NH_4HF_2$, more preferably HF. Mixtures of two or more of the above-listed fluorinating agents can also be applied. Generally, the concentration of the fluorinating agent in the solution is about 0.01 to about 3 mol/l, preferably about 0.1–2 mol/l.

The fluorinating conditions are such as to incorporate about 1 to about 10 (preferably about 2–5) weight-% F into the cooled, calcined catalyst. Generally, this requires a contacting time in step (3) of about 0 5 to about 12 hours (preferably about 1–8 hours), a contacting temperature of about 10 to about 90° C. (preferably about 24–40° C.), and a weight ratio of the solution of the fluorinating agent to the cooled calcined catalyst of about 0.5:1 to about 5:1 (preferably about 1:1 to about 3:1). The length of contacting period required will, of course, vary with the treatment conditions employed, such that for example, longer times would be appropriate at lower temperatures while shorter times would be required at elevated temperatures. The pressure can be atmospheric or higher, and the atmospheric conditions in the contacting vessel can be oxidative (e.g., air) or inert (e.g., $N_2$).

The contacting can be carried out by impregnation or partial impregnation (i.e., an ion-exchange technique) of the cooled calcined catalyst with the dissolved fluorinating agent, or by spraying the solution of the fluorinating solution onto the cooled calcined catalyst (e.g., in a rotating drier), or by any other effective method which is available to those skilled in the art. Those skilled in the art recognize that care should be taken to scrub or otherwise suitably treat any off-gases produced in the contacting step or in the subsequent drying step to prevent the release of substantial quantities of fluorine compounds from the process.

The thus-fluorinated calcined spent catalyst is then dried in step (4) so as to remove a substantial portion (preferably over 95%) of solvent (preferably water) from the catalyst. This can be done by any of the well known drying techniques, generally at a temperature of about 70–150° C. for a time period of about 0.5–20 hours. It is within the scope of this invention (presently not preferred) to carry out an additional calcining step, substantially at the conditions of calcining step (1), i.e., at about 500–700° C., for about 5 minutes to about 40 hours. Optionally, the fluorinated calcined catalyst is first washed with an aqueous liquid, preferably with water (by any of the well known washing techniques) before the drying step (4). Also, before the drying step (and preferably also before the washing step), excess liquid can be removed from the fluorinated spent catalyst by any of the well known liquid-solid separation techniques, such as by filtration, decantation, and the like.

In the second, presently less preferred, catalyst treatment process of this invention, the spent butane isomerization catalyst is first treated in step (A) with a solution of an effective fluorinating agent. The fluorinating agents and conditions are essentially the same as those described above for step (3).

Thereafter, the thus fluorinated spent catalyst is heated in drying step (B) under such conditions as to at least partially (preferably substantially) dry the fluorinated spent catalyst obtained in step (A). Preferred drying conditions are substantially the same as those described above for step (4). Optionally, the fluorinated catalyst is first washed (by any of the well known washing techniques) with an aqueous liquid, preferably water, before drying step (B). Also, before the drying step (and preferably also before the washing step) excess liquid can be removed from the fluorinated spent catalyst by any of the well known separation techniques, such as filtration, decantation, and the like.

The at least partially dried fluorinated catalyst is then calcined in step (C), at conditions which are essentially the same as those described for step (1). Preferably, the calcined fluorinated catalyst composition is then cooled to below about 500° C., substantially at conditions described for step (2).

The final catalyst composition, which has been prepared by one of the processes of this invention comprising steps (1)–(4) and (A)–(C), respectively, which is active as a pentane isomerization catalyst, generally contains about 0.01–10 weight-% Pt (preferably about 0.1–1 weight-% Pt), about 1–10 weight-% F (preferably about 2–6 weight-% F) and, optionally, about 0.01–2 weight-% Cl (preferably less than about 1 weight-% Cl). It may contain small amounts (preferably less than about 0.1 weight-%) of carbon.

In accordance with a particular embodiment of the present invention, a process for the isomerization of n-pentane to isopentane (2-methylbutane) is provided employing the fluoride-containing platinum on alumina isomerization catalyst prepared by one of the catalyst conversion processes described above. Thus, a pentane-containing feed is typically contacted with the substantially water-free, fluoride-containing platinum on alumina isomerization catalyst in a plug flow fixed bed reactor. Preferably, the catalyst is heated in a free hydrogen stream at about 300–800° F. prior to contacting with a n-pentane containing refinery feed (which generally also contains about 5–200 parts by weight of sulfur per million parts by weight of the feed). Process conditions for the pentane isomerization process are well known to those skilled in the art and have been described in the patent literature (e.g., U.S. Pat. No. 4,612,293). Preferred conditions for carrying out the isomerization process of the present invention include a temperature in the range of about 500–800° F., a pressure of about 150–1500 psig, a hydrogen to n-pentane volume ratio in the range of about 0.5:1 to about 10:1 (more preferably about 1:1 to about 3:1), and a liquid hourly space velocity of n-pentane in the range of about 0.2 to 6 (more preferably about 1–3) cc feed/cc catalyst/hour. Isopentane can be separated from unconverted n-pentane and by-products by conventional means.

The following examples are presented to further illustrate the invention and are not to be considered as unduly limiting the scope of the invention.

EXAMPLE I

This example illustrates the rejuvenation of a spent "1-8" butane isomerizing catalyst by the preferred catalyst treatment process of this invention comprising steps (1)–(4), described above.

The fresh I-8 catalyst (1/16" diameter extrudates) had been purchased from UOP, Inc., Des Plaines, IL, and had then been used in a commercial $C_4$ isomerization unit of Phillips Petroleum Company at its Borger, Texas refinery, until the catalyst had become substantially inactive. The spent I-8 catalyst contained about 0.2 weight-% Pt, about 3.4 weight-% Cl and about 0.12 weight-% carbon.

Samples of spent 1-8 catalyst (grey colored; ranging in weight from about 40 g to about 120 g) were calcined in a stream of air at various temperatures for various periods of time (as indicated in Table 1). The calcined catalyst samples were allowed to cool to room temperature and were then treated with aqueous solutions of hydrogen fluoride (HF) or ammonium bifluoride ($NH_4HF_2$) which contained about 3–3.5 weight-% F and had a pH of about 2–3. The weight ratio of the aqueous solution to the calcined catalyst was about 1:1 to about 3:1. The treatment of the calcined catalyst with the aqueous fluoriding solution was carried out in an ion-exchange mode (i.e., by soaking in excess solution), at a temperature of about 70–100° F. for several hours (generally about 1–10 hours).

Thereafter, the fluorinated catalyst samples were separated from the used aqueous fluoriding solution by filtration, the filter cakes were washed several times with deionized water, and the washed, rejuvenated catalyst samples were dried for about 16–18 hours, at a temperature of about 250° F. Detailed rejuvenation conditions are summarized in Table I. The rejuvenated spent 1-8 catalysts (exhibiting a creamy, off-white color) generally contained about 0.2 weight-% Pt, about 3.5 weight-% F, about 0.7 weight-% Cl and about 0.07 weight-% carbon.

EXAMPLE II

The dried rejuvenated catalyst samples, described in Example I, were tested for n-pentane isomerization activity at about 700–750° F. substantially in accordance with the test procedure described in Example II of U.S. Pat. No. 4,612,293. About 17 grams (about 20 cc) of each rejuvenated catalyst were loaded into a tubular, heated stainless-steel reactor (½ inch diameter), and were pretreated (activated) for several hours in a stream of 400–600 cc/minute hydrogen gas, at a temperature slowly rising from about 300–400° F. to about 680–750° F. under atmospheric pressure conditions. Thereafter, the reactor was pressurized with hydrogen gas to an operating pressure of about 480 psig, and liquid n-pentane (containing 5–200 ppm sulfur) was introduced at the top of the reactor and pumped through the catalyst bed at a rate of about 60 cc/hour. Hydrogen gas was passed through the catalyst bed (concurrently with the n-pentane feed) at a rate of about 25 liters $H_2$ per hour. Samples of the reactor effluent were taken at periodic intervals and analyzed by means of a gas chromatograph. Test results are summarized in Table I.

TABLE I

| Run | Calcination Temp. (°C.) | Calcination Time (Hrs.) | Fluorin. Agent | Isomeriz. Temp. (°C.) | Effluent Composition (Weight-%) Isopentane | n-Pentane[1] | Lights[2] | Heavies[3] | $iC_5/nC_5$ Ratio[4] |
|---|---|---|---|---|---|---|---|---|---|
| 1A | 500 | 20 | HF | 728 | 59.8 | 39.2 | 0.8 | 0.2 | 1.53:1 |
| 1B | 500 | 20 | HF | 730 | 59.7 | 39.3 | 0.7 | 0.3 | 1.52:1 |
| 1C | 500 | 20 | HF | 748 | 61.1 | 37.2 | 1.2 | 1.0 | 1.64:1 |
| 1D | 500 | 20 | HF | 741 | 61.0 | 35.3 | 2.4 | 1.3 | 1.73:1 |
| 1E | 500 | 20 | HF | 729 | 61.4 | 35.5 | 1.9 | 1.1 | 1.73:1 |
| 1F | 500 | 20 | HF | 712 | 61.2 | 36.9 | 1.2 | 0.8 | 1.66:1 |
| 1G | 500 | 20 | HF | 708 | 59.4 | 38.9 | 0.9 | 0.8 | 1.53:1 |
| 1H | 500 | 20 | HF | 690 | 56.9 | 41.8 | 0.6 | 0.7 | 1.36:1 |
| 2A | 500 | 4 | $NH_4HF_2$ | 706 | 9.6[6] | — | — | — | — |
| 2B | 500 | 4 + 40[5] | $NH_4HF_2$ | 708 | 52.6 | 44.2 | 2.4 | 0.8 | 1.19:1 |
| 2C | 500 | 4 + 40[5] | $NH_4HF_2$ | 711 | 54.6 | 41.9 | 2.8 | 0.7 | 1.30:1 |
| 2D | 500 | 4 + 64[5] | $NH_4HF_2$ | 718 | 62.3 | 34.5 | 2.2 | 1.0 | 1.81:1 |
| 2E | 500 | 4 + 64[5] | $NH_4HF_2$ | 716 | 25.5[6] | 73.7 | 0.1 | 0.7 | 0.35:1[6] |
| 3 | 500 | 4 | HF | 701 | 62.3 | 36.8 | 0.2 | 0.7 | 1.69:1 |
| 4A | 600 | 1.5 | HF | 729 | 60.2 | 37.9 | 1.1 | 0.8 | 1.59:1 |
| 4B | 600 | 1.5 | HF | 710 | 58.9 | 39.7 | 0.8 | 0.7 | 1.48:1 |
| 5A | 600 | 4 | HF | 713 | 45.1 | 54.0 | 0.2 | 0.7 | 0.84:1 |
| 5B | 600 | 4 | HF | 714 | 47.8 | 51.3 | 0.3 | 0.7 | 0.93:1 |
| 6 | 650 | 1.5 | HF | 717 | 58.9 | 40.0 | 0.5 | — | 1.47:1 |
| 7 | 650 | 0.5 | HF | 718 | 30.6 | 68.2 | 0.1 | 0.7 | 0.45:1 |
| 8 | 650 | 0.5 | HF | 723 | 59.6 | 38.9 | 0.9 | 0.6 | 1.53:1 |
| 9A | 650 | 0.5 | HF | 723 | 61.5 | 36.5 | 1.3 | 0.7 | 1.68:1 |
| 9B | 650 | 0.5 | HF | 721 | 62.1 | 36.4 | 1.0 | 0.6 | 1.71:1 |
| 9C | 650 | 0.5 | HF | 721 | 62.1 | 36.5 | 0.9 | 0.5 | 1.70:1 |
| 10A | 650[7] | 0.5 | HF | 722 | 60.0 | 38.0 | 1.4 | 0.7 | 1.58:1 |
| 10B | 650[7] | 0.5 | HF | 723 | 60.2 | 37.5 | 1.5 | 0.8 | 1.61:1 |
| 11A | 750 | 0.5 | HF | 713 | 50.7 | 48.2 | 0.4 | 0.6 | 1.05:1 |

TABLE I-continued

| Run | Calcination Temp. (°C.) | Time (Hrs.) | Fluorin. Agent | Isomeriz. Temp. (°C.) | Effluent Composition (Weight-%) Isopentane | n-Pentane[1] | Lights[2] | Heavies[3] | iC5/nC5 Ratio[4] |
|---|---|---|---|---|---|---|---|---|---|
| 11B | 750 | 0.5 | HF | 713 | 50.0 | 49.0 | 0.4 | 0.6 | 1.02:1 |
| 11C | 750 | 0.5 | HF | 731 | 54.6 | 44.2 | 0.5 | 0.7 | 1.24:1 |
| Control[8] | No calcining | | HF | 754 | 14 | — | — | — | — |
| Control[8] | No calcining | | HF | 719 | 7 | — | — | — | — |

[1] unconverted n-pentane feed
[2] cracked products with 4 or less C atoms per molecule
[3] oligomers with more than 5 C atoms per molecule
[4] weight ratio of formed isopentane to unconverted n-pentane
[5] calcined at 500° C. for 4 hours before fluorination, and calcined again for 40 and 64 hours, resp., after fluorination
[6] result believed to be erroneous
[7] calcined in nitrogen (instead of air)
[8] reactivated by the claimed method of U.S. Pat. 4,612,293

Test data in Table I demonstrate that the catalyst rejuvenation method of this invention produces a more active pentane isomerization catalyst than the method of U S. Pat. No. 4,612,293 (as per comparison of invention runs 1-11 with Control runs). Furthermore, these data indicate: (a) HF is a more effective fluorinating agent than $NH_4HF_2$ (ammonia bifluoride); (b) calcining at about 600-750° C. is quite effective and requires relatively short calcining times (see runs 6-10); (c) calcining after fluorination is not preferred because it generally results in undesirably high "lights" (cracked products) production; (d) an isomerization temperature of about 700-720° C. is presently most preferred for attaining a combination of high isopentane yield and low lights yield.

EXAMPLE III

This example illustrates a preferred procedure for converting larger amounts of a spent butane isomerization catalyst to an active pentane isomerization catalyst.

25,000 pounds of spent I-8 catalyst were pneumatically transferred from shipping drums into a calciner feed hopper. The catalyst was continuously introduced into a rotary calciner (18 inches diameter; 18 feet length) at a rate of 160 pounds per hour. The calciner was tilted about 0.75 degree and rotated at 1 RPM. These calciner settings gave a 30 minute residence time of the catalyst in the 650° C. hot zone. A counter-current stream of air swept HCl gas from the catalyst into a caustic scrubber where it was neutralized.

The calcined catalyst was screened so as to remove fines (less than 14 mesh) from the calcined catalyst.

Eighty pound batches of sieved catalyst were fed into a polyethylene container which contained enough of an aqueous, 3 weight-% HF solution to cover the entire catalyst batch. After 8 hours of soaking at about 90° F., the spent acid solution was drained through a valve located at the bottom of the soak container. The spent acid solution was neutralized with sodium carbonate to a pH of about 7 and then discarded. The separated HF-treated catalyst was washed by soaking it for about 5 minutes with deionized water, followed by draining of the wash water. This procedure was twice repeated.

The wet catalyst in the soak container was emptied into a 55 gallon polyethylene drum and pneumatically transferred to the hopper of the rotary calciner described above, which was now operated as a rotary drier at a temperature ranging from about 200° C. at the entrance to about 300° C. at the exit. The calciner tilt, rotary speed (RPM number) and residence time of catalyst were substantially the same as described for the calcining step. Wet catalyst which tended to stick to the rotary drier near the entry port was dislodged by "knockers". The dried catalyst was screened again to remove fines, and was then placed in drums. Water/HF vapors exiting from the drier were neutralized in a caustic scrubber (described above).

EXAMPLE IV

This example illustrates the less preferred catalyst rejuvenation method of this invention employing no pre-calcining step but a calcining step after fluorination.

The fluorination treatment of the spent I-8 catalyst (which had not been washed and/or calcined), and the subsequent washing and drying of the fluoride-treated catalyst were carried out substantially as described in Example I. However, in lieu of a calcining step before fluorinating, a calcining step after fluorination was carried out at about 500° C. for about 4-20 hours. Treating conditions and results of n-pentane isomerization tests (carried out essentially in accordance with the procedure described in Example II) are summarized in Table II.

TABLE II

| Run | Fluorin Agent | Calcination Temp (°C.) | Time (Hrs.) | Isomeriz. Temp (°C.) | Effluent Composition (Wt-%) Isopentane | n-Pentane[2] | Lights[2] | Heavies[2] | iC5/nC5 Raio[2] |
|---|---|---|---|---|---|---|---|---|---|
| 12A | HF | 500 | 3.5 | 705 | 48.2 | 50.0 | 1.0 | 0.8 | 0.96:1 |
| 12B | HF | 500 | 3.5 | 727 | 55.3 | 41.5 | 1.3 | 1.2 | 1.33:1 |
| 13A | $NH_4HF_2$ | 500 | 4 | 701 | 38.9 | 60.0 | 0.5 | 0.7 | 0.65:1 |
| 13B | $NH_4HF_2$ | 500 | 4 | 727 | 47.3 | 50.8 | 1.0 | 0.8 | 0.93:1 |
| 14A | HF | 500 | 3.5 + 17[1] | 707 | 53.0 | 43.8 | 2.4 | 0.8 | 1.21:1 |
| 14B | HF | 500 | 3.5 + 17[1] | 710 | 54.4 | 42.2 | 2.5 | 0.9 | 1.29:1 |

[1] the catalyst of runs 12A & B was calcined again at 500° C. for 17 hours
[2] see footnotes 1-4 of Table I Test data in Table II and a comparison with those of Table I indicate that the second rejuvenation method of this invention is more effective than the method of U.S. Pat. No. 4,612,293 (compare Table II with Control runs in Table I), but is generally less effective (in terms of high isopentane yield and low lights yield) than the preferred method of this invention comprising calcining before fluorination (compare data in Table II with those of runs 1-11 in Table I). Furthermore, the test data in Table II show that NH$_4$HF$_2$ was more effective than HF in this second rejuvenation method.

Reasonable variations and modifications which will be apparent to those skilled in the art, can be made within the scope of the disclosure and appended claims without departing from the scope of this invention.

That which is claimed is:

1. A process for converting a spent butane isomerization catalyst which comprises platinum and chlorine on an alumina support to an active catalyst for isomerizing n-pentane comprising the steps of:
   (1) calcining said spent butane isomerization catalyst at a temperature in the range of about 500° C. to about 700° C. for a time sufficient to remove a substantial portion of chlorine contained in said spent catalyst;
   (2) cooling the calcined spent catalyst obtained in step (1) to a temperature below about 500° C.;
   (3) treating the cooled calcined spent catalyst obtained in step (2) with a solution of at least one effective fluorinating agent under such conditions as to introduce fluorine into said cooled calcined spent catalyst; and
   (4) drying the fluorinated spent catalyst obtained in step (3) under such conditions as to obtain a substantially dry fluorinated catalyst which is active as a catalyst for isomerizing n-pentane to isopentane.

2. A process in accordance with claim 1, wherein said spent catalyst comprises about 0.01–10 weight percent platinum, about 1–10 weight percent chlorine, and about 0.05–0.5 weight-% carbon.

3. A process in accordance with claim 1 wherein said calcining is carried out in a free oxygen containing gas atmosphere at a temperature of about 600–750° C. for about 10 minutes to about 10 hours.

4. A process in accordance with claim 1, wherein said at least one effective fluorinating agent is selected from the group consisting of HF, NH$_4$F, NH$_4$HF$_2$, NH$_3$RF, NH$_2$R$_2$F, NHR$_3$F, NR$_4$F, and mixtures thereof, wherein R is a hydrocarbyl radical containing 1–6 carbon atoms.

5. A process in accordance with claim 4, wherein said at least one effective fluorinating agent is HF.

6. A process in accordance with claim 5, wherein said solution employed in step (3) is aqueous and contains about 0.01–3 mol/l of said at least one effective fluorinating agent.

7. A process in accordance with claim 1, wherein the fluorinating conditions in step (3) comprise a contacting time of about 0.5–12 hours, a contacting temperature of about 10–90° C., and a weight ratio of said solution to said cooled calcined spent catalyst in the range of 0.5:1 to about 5:1

8. A process in accordance with claim 1 comprising the additional step of washing the fluorinated spent catalyst obtained in step (3) with an aqueous liquid before step (4).

9. A process in accordance with claim 1 comprising the additional step of calcining the substantially dry fluorinated- catalyst obtained in step (4) at a temperature of about 500–700° C. for about 5 minutes to about 40 hours.

10. A process in accordance with claim 1 wherein said substantially dry fluorinated catalyst, which is active as a catalyst for isomerizing n-pentane to isopentane, comprises about 0.01–10 weight percent Pt and about 1–10 weight percent F.

11. A process for converting a spent butane isomerization catalyst which comprises platinum and chlorine on an alumina support to an active catalyst for isomerizing n-pentane comprising the steps of:
   (A) treating said spent butane isomerization catalyst with a solution of an effective fluorinating agent under such conditions as to introduce fluorine into said spent catalyst;
   (B) heating the fluorinated spent catalyst obtained in step (A) to a temperature below 500° C. so as to at least partially dry the fluorinated spent catalyst obtained in step (A); and
   (C) calcining the at least partially dried fluorinated spent catalyst obtained in step (B) at a temperature in the range of from about 500 to about 700° C. for a time sufficient to remove a substantial portion of chlorine contained in the at least partially dried fluorinated spent catalyst and to obtain a fluorinated spent catalyst which is active as a catalyst for isomerizing n-pentane to isopentane.

12. A process in accordance with claim 11, wherein said spent catalyst comprises about 0.01–10 weight percent platinum, about 1–10 weight percent chlorine, and about 0.05–0.5 weight-% carbon.

13. A process in accordance with claim 11, wherein said at least one effective fluorinating agent is selected from the group consisting of HF, NH$_4$F, NH$_4$HF$_2$, NH$_3$RF, NH$_2$R$_2$F, NHR$_3$F, NR$_4$F, and mixtures thereof, wherein R is a hydrocarbyl radical containing 1–6 carbon atoms.

14. A process in accordance with claim 13, wherein said at least one effective fluorinating agent is NH$_4$HF$_2$.

15. A process in accordance with claim 14, wherein said solution employed in step (A) is aqueous and contains about 0.01–3 mol/l of said at least one effective fluorinating agent.

16. A process in accordance with claim 11, wherein the fluorinating conditions in step (A) comprise a contacting time of about 0.5–12 hours, a contacting temperature of about 10–90° C., and a weight ratio of said solution to said cooled calcined spent catalyst in the range of 0.5:1 to about 5:1.

17. A process in accordance with claim 11, comprising the additional step of washing the fluorinated spent catalyst obtained in step (A) with an aqueous liquid before step (B).

18. A process in accordance with claim 11, wherein said calcining is carried out in a free oxygen containing gas atmosphere at a temperature of about 600–750° C. for about 10 minutes to about 10 hours.

19. A process in accordance with claim 11, wherein said fluorinated spent catalyst obtained in step (C) comprises about 0.01–10 weight percent Pt and about 1–10 weight percent F.

20. A process in accordance with claim 10, wherein said fluorinated catalyst comprises about 0.1–1 weight percent Pt, about 2–6 weight percent F., and about 0.01–2 weight percent Cl.

21. A process in accordance with claim 19, wherein said fluorinated spent catalyst comprises about 0.1–1 weight percent Pt, about 2–6 weight percent F, and about 0.01–2 weight percent Cl.

* * * * *